United States Patent [19]

Legocki et al.

[11] Patent Number: 5,221,623
[45] Date of Patent: Jun. 22, 1993

[54] USE OF BACTERIAL LUCIFERASE STRUCTURAL GENES FOR CLONING AND MONITORING GENE EXPRESSION IN MICROORGANISMS AND FOR TAGGING AND IDENTIFICATION OF GENETICALLY ENGINEERED ORGANISMS

[75] Inventors: Roman P. Legocki; Misuk Legocki; Aladar A. Szalay, all of Ithaca, N.Y.; Thomas O. Baldwin, Bryan, Tex.

[73] Assignees: Boyce Thompson Institute for Plant Research, Inc., Ithaca, N.Y.; Texas A & M University, College Station, Tex.

[21] Appl. No.: 382,255

[22] Filed: Jul. 19, 1989

Related U.S. Application Data

[63] Continuation of Ser. No. 888,746, Jul. 22, 1986, abandoned.

[51] Int. Cl.⁵ .................... C12N 15/74; C12N 15/90; C12N 15/05; C12N 15/33
[52] U.S. Cl. .................... 435/252.3; 435/69.1; 435/172.3; 435/320.1; 435/189
[58] Field of Search .................. 435/69.1, 189; 536/27

[56] References Cited

U.S. PATENT DOCUMENTS

4,851,335  4/1986  Baldwin ........................... 435/172.3
4,861,709  8/1989  Ulitzer et al. ......................... 435/6

OTHER PUBLICATIONS

Schindler, F. J., 1964, Dissertation, University of Pennsylvania Graduate School of Arts and Sciences, 139 pages.
Root, M., 1988, *BioScience*, 38(11):745–747.
Baldwin, T. O., et al., 1984, in *Analytical Applications of Bioluminescence and Chemiluminescence*, Academic Press, 101–104.
Dunlap, P. V., et al., 1985, *Journal of Bacteriology*, 164(1):45–50.
Shaw, J. J., et al., 1986, *Bio/Technology*, 4: 560–564.
Potter, H., et al., 1984, *Proceedings, National Academy of Sciences USA* 81: 7161–7165.
Nealson, K. H., et al., 1977, *Archives of Microbiology*, 112: 9–16.
Haygood, M. G., et al., 1986, *Gene*, 45: 203–208.
Schmettever, G., et al., (1986), Journal of Bacteriology 167(1):411–414.
Legocki, R. P., et al., 1984, Proc. Natl'l Acad. Sci. USA 81: 5806–5810.
Engebrecht, J., et al., 1985, Science 227: 1345–1347.
Stüber, D., and H. Bujard, 1981, Proc. Nat'l Acad. Sci. USA 78(1): 167–171.
Shaw, J. J., et al., 1985, American Phytopathological Society Annual Meeting, Abstract No. 88.

*Primary Examiner*—Robert A. Wax
*Assistant Examiner*—William W. Moore
*Attorney, Agent, or Firm*—Ralph R. Barnard

[57] ABSTRACT

A host microorganism is genetically and stably modified by the insertion into any of its non-essential chromosomal location of a non-homologous, recombinant foreign DNA fragment, maintaining an insertion of a luxAB gene of a selected bioluminescent bacterium such as V. harveyi, such that the expression of the luxAB genes causes the production of a luciferase enzyme which, in turn, catalyzes a light-emitting reaction in the presence of the appropriate substrate. X-ray film can be used to quantify the light being emitted from a microorganism through the use of plural droplets containing the same microorganism, each with a known and related cell (or plasmid) count.

12 Claims, 11 Drawing Sheets a b c d e f g h i j mw cont. a b c d e f g h i j mw

FIG. 3A
FIG. 3B
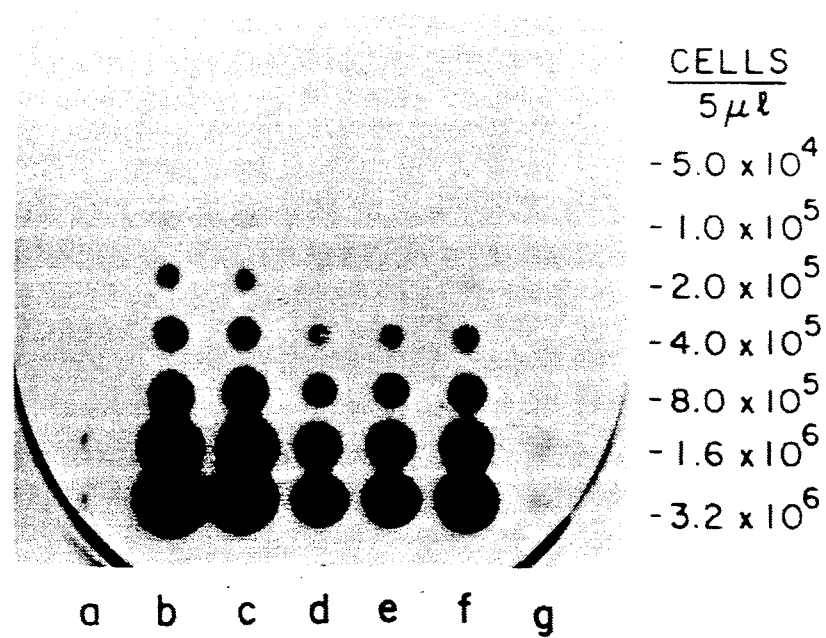

a  b

USE OF BACTERIAL LUCIFERASE STRUCTURAL GENES FOR CLONING AND MONITORING GENE EXPRESSION IN MICROORGANISMS AND FOR TAGGING AND IDENTIFICATION OF GENETICALLY ENGINEERED ORGANISMS

This invention is a subject invention of a Research Grant No.: DMB 8411460 from the National Science Foundation to Boyce Thompson Institute for Plant Research, Inc. and a Research Grant No: DMB 8510784 from the National Science Foundation to Texas A & M University.

This is a continuation of application Ser. No. 06/888,746, filed Jul. 22, 1986, now abandoned.

BACKGROUND OF THE INVENTION

Microorganism markers are a necessary tool in the study, the manipulation, and the control of gene expression in the fields of research, production and control of microorganisms. This invention relates to the use of the lux AB gene cluster of *Vibrio harveyi*, a luminescent marine bacterium, as such a marker and/or tag.

Naturally occuring microorganisms need to be tagged or marked for monitoring their gene activity whenever that is necessary or desired for whatever reason. Moreover, ways need to be developed to label each genetically engineered organism so its use, identity and fate can be monitored in the field. This would greatly simplify studies of an organism's escape, survival, multiplication and dispersal and may help in tracking the movement of DNA among organisms in the environment.

The isolated lux AB gene cluster of *V. harveyi* was selected as a marker or tag because it was found to have several advantageous features including an unrestricted host background and an unrestricted growth medium requirement. In this respect, the lux AB genes of *V. harveyi* are different from the lac Z gene of *Escherichia coli*, a commonly used expression marker which, when fused with a promoter, has a restricted host background (i.e. it can be only used in microorganisms with no ability to utilize lactose). Most microorganisms will utilize lactose. Moreover, the cells containing lac Z fusions have to be grown in minimal media (a restricted number of components) in order for the lac Z product (B-galactosidase) to be detected. An especially attractive reason for using the lux AB gene of *V. harveyi* as a marker or tag for a microorganism is that it provides for the noninvasive measurement of the presence and absence of the marker through the presence of absence of bioluminescence as a measure of gene expression in vivo. The magnitude of bioluminescence is readily quantizible by new and known light detection techniques. The lac Z marker system does not have these capabilities. It uses a chemical substrate the color and intensity of which is the indicator of the reaction rate within the bacterium.

As known in the prior art, light is produced in *E. coli* cultures that contain seven lux genes cloned from another and different marine bacterium, *Vibrio fischeri*. (See an article entitled "Measuring Gene Expression with light" by Engebrecht, et al., Science, Volume 227, Mar. 15, 1985, pages 1345-1347). Therein it states in the abstract:

These lux genes were disconnected from their native promoter and inserted into the transposon mini-Mu. The resulting transposon, mini-Mu lux, could induce mutations by insertional inactivation of a target gene, and the lux DNA was oriented to align target gene transcription with that of the lux genes. Genes in *Escherichia coli* and *Vibrio parahaemolyticus* were mutagenized, and mutants containing transposon-generated lux gene fusions produced light as a function of target gene transcription.

However, the teachings of Engebrecht, et al. have limited application to the marking and tagging of microorganisms because all seven of the lux genes in V. fischeri are required for light production and the large size of this gene cluster increases the chance of its inactivation by mutation. Furthermore, it is not known whether the lux gene cluster of *V. fischeri* could reliably function as a measure of activity in microorganisms such as Bradyrhizobium. However, it does so function in *E. coli* and it does provide its own substrate for the production of light.

A new avenue for research and development in this field was presented by an article entitled "Cloning of the Luciferase Structural Genes from *Vibrio harveyi* and Expression of Bioluminescence in Escherichia coli" by Baldwin, et al., appearing in Biochemistry, 1984, Vol. 23, Pages 3663-3667. Therein bacterial luciferase in the luminous marine bacterium *Vibrio harveyi* was discussed as follows:

"The DNA encoding the luciferase alpha and beta subunits in the luminous marine bacterium Vibro harveyi (strain 392) is contained within a 4.0-kilobase HindIII fragment. DNA from V. harveyi was digested with HindIII, and the resulting fragments were inserted into the HindIII site of plasmid pBR322. The recombinant plasmids were introduced by transformation into Escherichia coli RR1. The colonies were supplied with n-decanal, the substrate for bioluminescence reaction, and 12 colonies (of ca. 6000 total) were observed to luminesce brightly. One of the recombinant plasmids, pTB7, has been studied in detail. The high level of expression of bioluminescence in pTB7 was the result not of native V. harveyi promoters but rather of a promoter in pBR322 which is within the tetracycline resistance gene but oriented in the direction opposite to the transcription of the tetracycline gene."

The recombinant plasmid vector pTB7 is available from the Agriculture Research Service Patent Collection, Northern Research Center, Peoria, Ill., 61604 and has been given the designation NRRL B-15231.

While the Baldwin et al. article describes the use of the lux AB genes of *V. harveyi* to select the recombinant plasmid vectors pTB7 in *E. coli* as stated, it is clear that it does not teach or show the isolation of those recombinant DNA vectors from the E. coli by any means for the purpose of establishing a marker or tag in *E. coli* or any other organism as a measure of gene expression. The recombinant plasmid vector pTB7 was isolated only for the purpose of cloning the luciferase gene lux AB. U.S. Pat. No. 4,581,335, inventor Thomas O. Baldwin, dated Apr. 8, 1986, which relates to the same research as the Baldwin et al. article, supplements the report by suggesting that the plasmid vector pTB7 be transferred to a host *E. coli* such as *E. coli* RR1. The transformed *E. coli* is given the designation *E. coli*/pTB7 and is deposited at the same place and under the same designation. The type of transformation involved is the transfer of the plasmids pTB7 through and within the cell walls of the E. coli without insertion of the same into the chromosome of the E. coli. The plasmid pTB7 replicates outside of the chromosome of E. coli.

SUMMARY OF THE PRESENT INVENTION

The bioluminescence genes lux AB contained on the plasmid pTB7 in E. coli RR1 cannot be transferred to any other microorganism, because this plasmid will not replicate in any bacterium other than E. coli. The teachings of this invention involve a transfer of the lux AB genes into any Gram-negative microorganism by conjugation using the mob (ori T) DNA fragment of RP4, and insertion of said genes into the chromosome of the same microorganism, thus providing a genetically stable modification of the same microorganism here and after referred to as "host" or "target organism".

When the teachings of the present invention involve the transfer of the lux AB genes to Gram-positive bacteria, a non-conjugal transfer of this DNA is carried out by either calcium-mediated transformation of competent bacterial cells or by the electroporation technique, as referred to below.

Prior to the present invention there were no teachings of transferring the lux AB genes to any microorganism other than E. coli, and no teaching of inserting said genes into the chromosome of any microoganism, including E. coli.

As part of the teachings of the present invention the inventors herein were able to modify plasmid vector pTB7 to make what they call a promoter-activated light emission vector herein identified as pPALE001. Specifically, in the construction of pPALE001, a 0.6 kb SalI-HindIII fragment of pBR322 and a 0.3 kb HindIII-SalI fragment of V. harveyi DNA were deleted to form a single promoter-cloning site SalI, located about 130 bp upstream from the translational initiation codon of lux A. Also, the neomycin phosphotransferase gene (Km) was excised from plasmid pREV1000 with HindIII-AvaI and cloned into a BglII site of pPALE001 by blunt-end ligation. Even though the Pl promoter of pBR322 was deleted from pPALE001, the resulting plasmid did express detectable bioluminescence at about 1% level of that of pTB7. To eliminate this readthrough from upstream sequences, trp A transcription terminator (Pharmacia) was ligated into the XmaIII site of pPALE001 located about 0.3 kb upstream of the promoter-cloning site.

The plasmid vector pPALE001 is a promoterless source of lux AB genes and is used in the present invention to clone a promoter from the selected microorganism of interest, upstream of the lux AB genes to control the luciferase expression. Since pPALE001 replicates in E. coli only, the cloning of a promoter from the microorganism of interest is carried out in E. coli as the first step of the present invention. As described hereinafter, a mobilizable plasmid vector must be especially constructed for its use in the transfer of the promoter lux AB gene fusion from the plasmid vector pPALE001 to the microorganism of interest. For example, the mobilizable plasmid vector pMR19 was constructed for the specific purpose of inserting a promoter-lux AB gene fusion into the chromosome of B. japonicum. The plasmid pMR19 contains a 13.5 kb fragment of B. japonicum chromosome, and on this basis it is capable of inserting any foreign genes placed within said homology, including the above promoter—lux AB gene fusion, specifically into the B. japonicum chromosome by double homologous recombination. It is important to note that the 13.5 kb chromosomal homology fragment of pMR19 can be easily removed with the restriction enzyme KpnI and replaced with a chromosomal fragment of any other Gram-negative bacterium and thus it will mediate the insertion of the bioluminescene genes into any other bacterial chromosome.

The teaching of the present invention including the step of excising with AvaI the DNA fragment containing a promoter-lux AB gene fusion from all other genes as a part of preparing said fragment to be a part of the carrier vector, e.g., pMR19 for B. japonicum, for insertion into the chromosome of any target microorganism. Specifically, the carrier vector is prepared by cutting "non-essential" or "silent" DNA pieces out of the chromosome of the target microorganism. The promoter-lux AB gene fusion is then inserted into this fragment, and the DNA carrying the promoter-lux AB gene fusion is inserted into the chromosome of the target microorganism by homologous recombination. Homologous recombination is a known technique for introducing foreign DNA into the chromosome of a microorganism. For example, an article by Legocki, R. P., Yun, A. C. and Szalay, A. 1984, Proc. Natl. Acad. Sci USA 81, pg. 5806-5810, illustrates the insertion of a promoter-marker gene fusion into a Rhizobium chromosome through the use of homologous recombinations. The subsequent transformation of the target microorganism with the pMR19-like plasmid carrying the promoter-lux AB fusion involves two general questions. First, what transformation technique should be used to cause the pMR19-like plasmid to cross the cell wall of the target microorganism, and second, will this plasmid replicate episomally or should it be integrated into the chromosome?

As is known to those skilled in the art access through the cell wall of the microorganism maybe gained by (1) soaking the cells in calcium chloride (calcium precipitation); (2) subjecting the cells to electrical shock (electroporation), or (3) utilizing a mobilizable plasmid following the techniques well known to those skilled in the art and illustrated in an article by Simon, R. Priefler, U. and Puhler, A., at pages 98-106 of a book entitled *Molecular Genetics of the Bacteria-Plant Interaction* by Springer-Verlag Berlin Heidelberg, 1983 Dr. Alfred Puhler, Editor.

The transformation of the promoter-lux AB gene fusion into any host microorganism such as B. japonicum for use as a marker or tag of gene expression requires an assured technique for access through the cell wall of the microorganism and a mechanism for a stable insertion of the fragment containing the lux AB fusion into the chromosome of the host microorganism such as B. japonicum. Accordingly, it is essential to the teachings of the present invention that a mobilizable plasmid (a carrier vector) be especially made for the host (target) microorganism which will pass through the cell wall by conjugation, and through homologous recombination will insert the promoter-lux AB gene fusion stably into the chromosome of the host microorganism. The technology for the construction of such a mobilizable plasmid carrier vector, established and known to those skilled in the art is illustrated by the Legocki, et al. and Simon, et al. publications. The teaching of this invention is that foreign DNA to be circularly inserted into the chromosome of the host microorganism using homologous recombination is a promoter-lux AB gene fusion, where the promoter comes from the same host microorganisms of interest, and lux AB genes come from *V. harveyi*.

Specifically, a mobilizable insertional plasmid such as pMR19 mediates a stable insertion of the promoter-lux AB gene fusion into the procaryotic organism such as *B. japonicum*. This plasmid comprises a DNA segment including first and second DNA portions containing DNA homologous to corresponding portion of the chromosome of the microorganism such as *B. japonicum*, with the first and second DNA portions oriented in relation to each other in the same manner as said homologous chromosomal DNA portions in *B. japonicum*, and a third DNA portion containing the promoter-lux AB gene fusion located between and covalently bonded to the first and second DNA portion.

The mobilization plasmid pMR19 used by the invention herein to insert the lux AB gene fusion into the chromosome of *B. japonicum* using the homologous recombination technique described herein is on patent restricted deposit (Budapest Convention) with the U.S. Department of Agriculture, Northern Regional Research Center, NRRL 1815, North University Street, Peoria, Ill., 61604, and assigned accession number NRRL B-18081. The mobilization plasmid pREV1000 may be used to insert the lux AB gene fusion into the chromosome of stem Rhizobium BTAil using the homologous recombination technique described herein and is on patent restricted deposit (Budapest Convention) with the aforesaid NRRL under accession No. NRRL B-153-19. Both pMR19 and pREV1000 plasmids contain the mob (ori T) DNA fragment that can be isolated from RP4 of *E. coli* as described in the above mentioned article of Simon, et al. (1983). The mob sequences are used in the present invention to establish an efficient conjugal transfer of a plasmid containing the promoter-lux AB gene fusion from *E. coli* to any Gram-negative bacterium, as exemplified for *B. japonicum* using the plasmid pMR19.

In accordance with the present invention, the fragment including the promoter-lux AB gene fusion may be inserted as a marker or tag into the chromosome of any Gram-negative bacterium. Cyanobacteria and photosynthetic microorganisms are other examples. The appropriate chromosomal homology region on this mobilizable plasmid to mediate insertion of the promoter-lux AB gene fusion into the chromosome of a particular microorganism will have to be attached for each separate and distinct microorganism.

Conjugal transfer of a mobilizable plasmid vector (herein pMR19 containing the promoter-lux AB gene fusion) from *E. coli* to *B. japonicum* is a known straightforward procedure that has been described in detail by Jagadish and Szalay, Mol. Genet. (1984), 196:290-300. Referring to paragraph 2 of page 292 of that paper, the bacterial conjugation for the transfer of lux AB- containing plasmid DNA for insertion into the selected bacterium is accomplished as follows: donor *E. coli* and the recipient bacterium of interest are grown separately in the appropriate media at 30° C. and are mixed at approximately equal cell numbers ($1-1.5 \times 10^9$ cells). The mixture is centrifuged and resuspended in 100 ml of the culture medium, and 50 ml of this suspension is was spotted onto sterile filters (0.45 mm, GAG Golman Sciences, Inc.) placed on the culture medium. Following incubation at 30° C. for 24 hours the cells are removed from the filter surface using a sterile toothpick washed in 5 ml of minimal medium and resuspended in 1 ml of fresh minimal medium. Undiluted or serially diluted samples are plated onto appropriate selective plates for growth of transconjugants. While the transfer of promoter-lux AB gene fusions to host microorganism in the present invention is mediated by mob genes, contained e.g. on the plasmid pMR19, via conjugal transfer, and thus is limited to Gram-negative bacteria, it should be clear that the same teachings of this invention apply to Gram-positive bacteria where the other two methods of cell transformation, listed above, should be used.

In addition to pPALE001, another plasmid vector, known as pFIT001, has been constructed which contains lux AB genes in accordance with the teachings of the present invention. In pFIT001, the lux AB genes are expressed constitutively from the Pl promoter of pBR322 plasmid vector. pFIT001 is constructed by modifying plasmid vector pTB7. Specifically: (1) the EcoRI site, located downstream (at the 3' end) of the 4.0 kb *V. harveyi* DNA fragment in the pBR322 region is inactivated by blunt ending; (2) the HindIII site located downstream (at the 3' end) of the 4.0 kb *V. harveyi* DNA fragment is inactivated by blunt ending.

*E. coli* carrying derivatives of pFIT001 with DNA inserts in the unique EcoRI site located in lux B form "dark" colonies that are readily distinguished from the bioluminescent or "bright" colonies carrying the original plasmid. Due to its simplicity, the pFIT001 is used as a common cloning vehicle for rapid visualization of plasmid clones carrying inserts. Furthermore, a single HindIII site in pFIT001, located between the Pl promoter and lux A, is suitable for testing DNA fragments for the presence of transcriptional terminators based on bioluminescence.

While the technical studies described herein were done with the lux AB genes of a biolumenscent bacterium *V. harveyi* as made available from the plasmid vector pTB7, it is clear that should another bioluminescent bacterium (such as *V. fischeri*) be of interest and should one wished to use the lux AB genes (only) of that other bioluminescent bacterium, one could proceed as described in a publication commented on herein above by Baldwin, et al., Biochemistry 1984, 23 3663. Essentially a plasmid vector (equivalent to pTB7) would have to be cloned in E. coli containing the lux AB genes of the selected bioluminescent bacterium (such as *V. fischeri, photobacterium, leiognathi, P. phosphoreum* or the terrestrial bacterium xenorhobdys).

The control and regulation of gene expression can be readily analyzed in vivo using promoter-lux AB fusions by a variety of simple methods, including a new technique described herein as "luxdot".

It is a primary object of the present invention to teach the genetically stable modification of a host microorganism by the insertion in one of its non-essential chromosomal locations of a DNA fragment containing lux AB genes of a selected bioluminescent bacterium such as *V. harveyi*, fused to a selected promoter isolated from the host microorganism, wherein the non-homologous fragment is stably reproduced as a part of the chromosome of the cells of the modified host microorganism as they divide in a growth medium.

It is another object of the present invention to teach the genetically stable modification of a host microorganism by the insertion in one of its non-essential chromosomal locations of a fragment containing lux AB genes of a selected bioluminescent bacterium such as *V.*

*harveyi* fused to a selected promoter isolated from the host microorganism wherein the non-homologous fragment is stably reproduced as a part of the chromosome of the cells of the modified host microorganism as they divide in a growth medium and the gene expression of such microorganism triggers the production of luciferase which, in turn emits blue-green light in the presence of aldehyde as a measure of gene expression and to serve as a marker or tag for the modified microorganism.

It is another object of the present invention to teach the genetically stable modification of any host microorganism by the insertion in one of its non-essential locations of a fragment containing lux AB genes of a selected bioluminescent bacterium such as *V. harveyi* fused to a selected promoter isolated from the host microorganism wherein the non-homologous fragment is stably reproduced as a part of the chromosome of the cells of the modified host microorganism as they divide in any growth medium known to support growth of the host microorganism in its unmodified form.

It is another object of the present invention to teach the genetically stable modification of any host microorganism by the insertion in one of its non-essential chromosomal locations of a fragment containing lux AB genes of a selected bioluminescent bacterium such as *V. harveyi* fused to a selected promoter isolated from the host microorganism wherein the non-homologous fragment is stably reproduced as a part of the chromosome of the cells of the modified host microorganism as they divide in a growth medium (normal to the unmodified host microorganism) and the gene expression of such microorganism triggers the production of luciferase which, in turn emits blue-green light in the presence of aldehyde as a measure of gene expression and to serve as a marker or tag for the modified microorganism.

It is another object of the present invention to teach the genetically stable modification of a host microorganism by the insertion in to one of the non-essential chromosomal locations of a fragment containing lux AB genes of a selected bioluminescent bacterium such as *V. harveyi* fused to a selected promoter isolated from the host microorganism wherein the non-homologous fragment is stably reproduced as a part of the chromosome of the cells of the modified host microorganism as they divide in a growth medium and the gene expression of such microorganism triggers the production of visible light in the presence of aldehyde as a measure of such activity without the need for drug markers, dyes or other indicators.

It is another object of the present invention to teach the genetically stable modification of a host microorganism by the insertion in one of the non-essential chromosomal locations of a fragment containing lux AB genes of a selected bioluminescent bacterium such as *V. harveyi* fused to a selected promoter isolated from the host microorganism wherein the non-homologous fragment is stably reproduced as a part of the chromosome of the cells of the modified host microorganism as they divide in a growth medium and the gene expression of such microorganism maybe monitored by the production of visible light in the presence of aldehyde as a measure of such activity without any harm or destruction to the living cells or organism.

It is another object of the present invention to teach the genetically stable modification of a host microorganism by the insertion in one of the non-essential chromosomal locations of a fragment containing lux AB genes of a selected bioluminescent bacterium such as *V. harveyi* fused to a selected promoter isolated from the host microorganism wherein the non-homologous fragment is stably reproduced as a part of the chromosome of the cells of the modified host microorganism as they divide in a growth medium and the gene expression of such microorganism causes the production of visible light in the presence of aldehyde and the intensity of the light as a measure of gene expression can be determined by any one of several simple and rapid methods including: visual assessment by the naked eye, brief exposure to X-ray films, the use of a liquid scintillation counter and the use of in vitro and in vivo luciferase enzyme assays as well as a new and novel light-quantifying method known as luxdot and further described herein.

It is another object of the present invention to teach the genetically stable modification of any replicative DNA forms (bacteriophages, viruses, cells and other living organisms) by the insertion in one of the non-essential chromosomal locations a fragment containing lux AB genes of a selected bioluminescent bacterium such as V. harveyi fused to a selected promoter isolated from the host microorganism wherein the non-homologous fragment is stably reproduced as a part of the chromosomal components of the cells of the modified host microorganisms as they divide in a growth medium and the gene expression of such microorganism causes the production of visible light in the presence of aldehyde and the intensity of the light as a measure of gene expression can be determined for any of the following purposes:

1. The protection and identification of the modified microorganism.
2. The detection of gene expression signals, including regulatory signals of the modified microorganism.
3. The tracing of tumorous growth and cell migration by tracing a modified microorganism.
4. The tracing of modified soil microorganisms and monitoring of their interaction with plants and other organisms.

It is still another object of the teachings of the present invention to provide a modified form of plasmid vector pTB7 which may be used to make a promoter activated light emission vector herein identified as pPALE001 on deposit with Agricultural Research Service, USDA, Peoria, Ill. 61604 under accession number NRRL B-18082 where said pPALE001 has many advantages as a marker or a tag because it obtains its promoter from the modified host microorganism into which it is inserted within a non-essential chromosomal location and the resulting bioluminescence is a measure of the occurance of the microorganism and magnitude of that activation is the measure of promoter strength and of gene expression in general.

It is still another object of the teachings of the present invention to provide a modified form of plasmid vector pTB7 which may be used to make a common cloning vehicle for rapid visualization of plasmid clones carrying inserts herein identified as pFIT001 on deposit with Agricultural Research Service, USDA, Peoria, Ill. 61604 under accession number NRRL B-18080 and furthermore having a single HindIII site located between the Pl promoter and lux A gene suitable for testing DNA fragments for the presence of transcriptional terminators based on bioluminescense.

It is an additional object of the teachings of the present invention to provide a new and improved method for quantizing the light emitted from biological material using the exposure of x-ray film by a plurality of droplets of said biological material wherein each of the plural droplets contains a known count of cells (or plasmids) of said biological material and each related droplet is a diluted sample with a related count of cells or plasmids which is based on the scale which has been selected for the purpose of quantizing the magnitude of the light.

BRIEF DESCRIPTION OF THE DRAWINGS

FIGS. 3A, 3B, 3C and 3D are separate panels illustrating the methods used to monitor gene expression by bioluminescence following the teachings of this invention.

DETAILED DESCRIPTION OF THE INVENTION

Figure 1A:
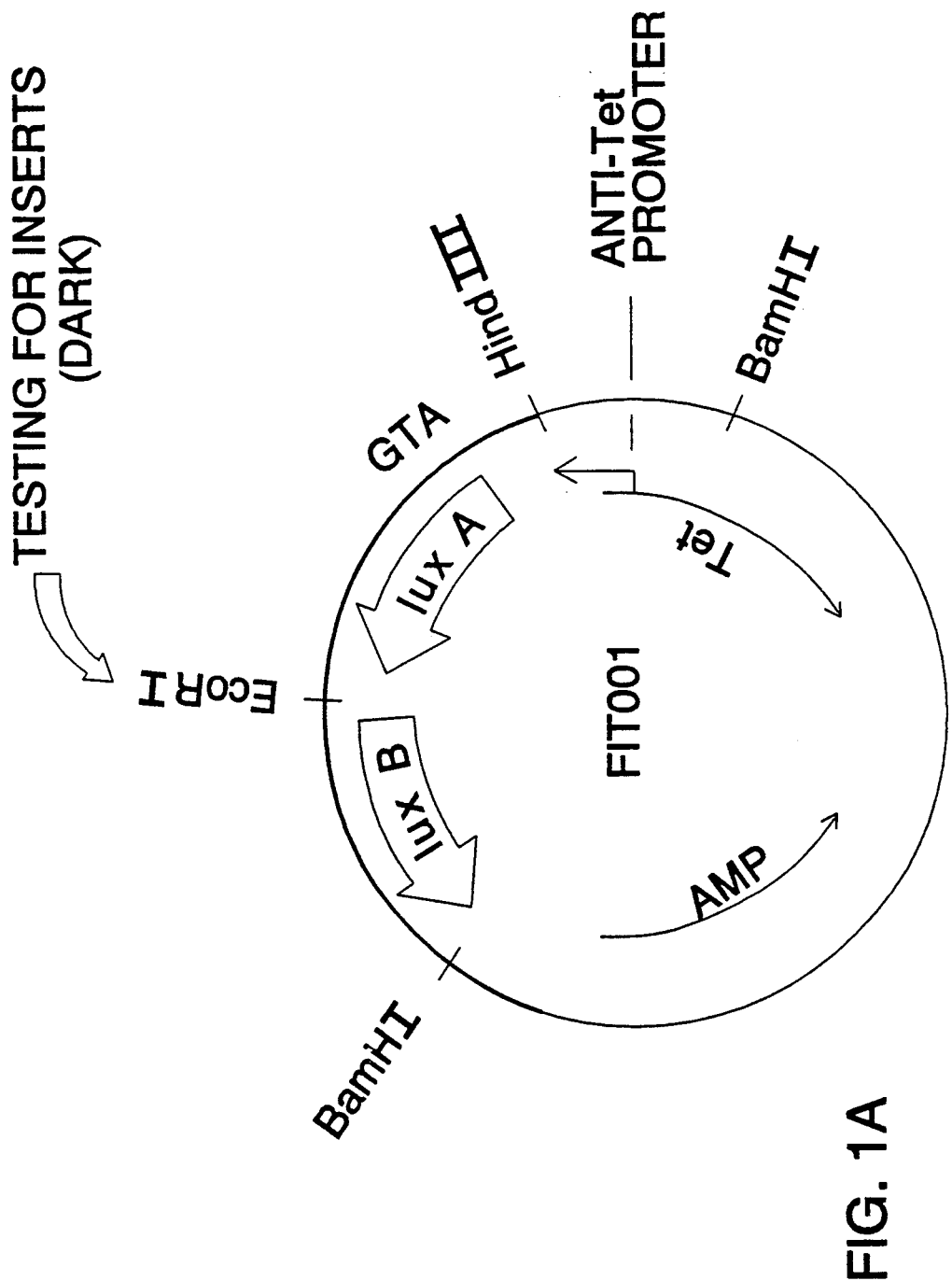
FIGS. 1A, 1B AND 1C illustrate plasmid vectors pFIT001, pPALE001 and pMR19 respectively.

The "Luxdot" system disclosed and taught herein is novel and has high utility. As stated, a key teaching herein is that the lux AB genes of *V. harveyi* can be stably inserted in the chromosome of a wide range of microorganisms without altering the growth medium composition in which that microorganism will grow and the gene expression of that modified microorganism may be measured by the release of light at a sensitivity level measurable with femtomoles of luciferase and within a few seconds (in vivo.) One of the many ways to measure the intensity of released light is to direct the light onto x-ray film. The developed film will give a relative measurement of the intensity of the produced light. Since the intensity of the light which is produced and described herein above is a measure of the rate of gene expression, it is extremely important that the intensity of the released light be quantified. The novel technique to accomplish this quantization which is described herein has a very high degree of utility and simplicity.

The microorganism which has been modified by the stable insertion of a promoter-lux AB fusion in a nonessential location within its chromosome following the teachings of the present invention, or one that harbors this gene fusion on a plasmid, is grown in liquid media to mid or late log phase, and about 1-5 ul volume ($10^7$-$10^8$ cells) are pelleted by centrifugation. Cells are resuspended in 0.1 ml of water on ice and dilutions were made in water to inhibit cell division. Following the determination of cell numbers with a hemocytometer plural dilutions are made of the modified microorganism so that the ratio of cells in a 5 ul droplet of each dilution is known and then the plural 5 ul droplets of each dilution are placed in an order based on the degree of dilution (or cell copy number) on the bottom of an empty plastic Petri dish. A streak of n-decanal is applied to the inner side of the lid and the covered Petri dish is exposed to an X-ray film at room temperature. The exposure time can vary between a few seconds and several hours, depending on the promoter strength, the copy number of the promoter-lux AB gene fusion and the number of cells in a droplet. The light intensity recorded by the X-ray film from the plural 5 ul droplets representing different dilutions and cell numbers in accordance with the selected scale represents the quantified gene expression with the modified microorganism as represented by the activation of the promoter lux AB gene fusion.

The selection of 5 ul droplets rather than another volume within limits is a matter of choice and the important point is that the droplets from the high concentration of potentially light-emitting cells (or plasmids) to the lowest concentration be known in number of cells (or plasmids) and follow the selected scale of the potentially light-emitting cells. The droplets must be small enough to maintain themselves as a cohesive drop and form a column of droplets of scaled dilutions (and scaled numbers of potentially light-emitting cells or plasmids). Plural columns of droplets, with each column representing a different modified microorganism in plural dilution (or cell count) may be arranged as grid in a single Petri dish. A primary teaching of the Luxdot system is that each droplet contains a known number of potentially light-emitting cells where the light released is quantified by simultaneously sampling plural droplets having cell (or plasmid) counts which are related to a selected side where each droplet is placed in a selected location (column and/or grid) on a flat surface of the Petri dish (or the equivalent) and the X-ray film is placed immediately outside the Petri dish (or its equivalent) to record the light emission. If the plural droplets are placed in columns and/or in a grid on the bottom of the Petri dish, the X-ray film may be placed right under the Petri dish to record the light emission from the plural droplets. If the plural droplets are small enough to adhere to the underside of the Petri dish cover in columns and/or a grid then the X-ray film may be placed on the top of the Petri dish cover. This system for quantifying the amount of light being emitted from plural droplets of a known number of biological cells has broad application. While the system was first used in making light measurement based on emissions resulting from the stable insertion of the lux AB genes of *V. harveyi* into the chromosomes of a wide range of microorganisms, the Luxdot system may be used for quantifying light emission from all kinds of biological material which emits light as long as the magnitude of the light is directly related to the number of cells (or plasmids) in the biological material.

The understanding of the genetic involvement of Rhizobium spp. in their symbiosis with legumes, leading to the formation of nodules and nitrogen fixation, has increased substantially in recent years. The following publications are made of reference: (Ruvkun, G. B. & Ausubel, F.M. (1980) Proc. Natl. Acad. Sci. USA 77, 191-195; Banfalvi, A., Sakanyan, V., Koncz, C., Kiss, A., Dusha, II. & Kondorosi, A., (1981) Mol. Gen. Genet. 184, 318-325; Prakash, R. K., Schilperoort, R. A. & Nuti, M.P. (1981) J. Bacteriol. 145, 1129-1136; Long, S. R., Buikema, W. J. & Ausubel, F.M. (1982) Nature (London) 298, 485-488. Since the initial identification of the nitrogen fixation (nif) and nodulation (nod) genes in rhizobia, their promoter regions have been fused to the lac Z gene of *E. coli* and measured for expression and regulation by the beta-galactosidase enzyme assay (see Miller, J. H. (1972) Experiments in Molecular Genetics (Cold Spring Harbor Laboratory, Cold Spring Harbor, NY), 2nd Ed. p. 352). Both transcriptional and translational fusions were used to detect and quantify the activation of R. meliloti nifh promoter by the nif A gene product of klebsiella pneumoniae (Sundaresan, V., Jones, J. D. G., Ow, D. W. & Ausubel, F. M. (1983) Nature (London) 301, 728–732.), to monitor the expression of the regulatory nif LA and gln ALG operons of K. pneumoniae, and to show that a chromosomally integrated nif H promoter-lac Z fusion is regulated in trans with the native nif locus in stem Rhizobium BTAi1. Reference is made to: Drummond, M., Clements, J., Merrick, M. & Dixon, R. (1983) Nature (London) 301, 302–307; Ow, D. W. & Ausubel, F. M. (1983) Nature (London) 301, 307–313; and Legocki, R. P., Yun, A. C. & Szalay, A. A. (1984) Proc. Natl. Acad. Sci. USA 81, 5806–5810. Recent studies indicated that expression of the R. meliloti nod ABC genes is activated by root exudates and by the nod D gene product, as evidenced by beta-galactosidase measurements using nod C and nod D promoter-lac Z gene fusions (Mulligan, J. T. & Long, S. R. (1985) Proc. Natl. Acad. Sci. USA 82, 6609–6613).

Herein we teach the use of the bacterial luciferase genes lux AB from V. harveyi to monitor the activity of procaryotic promoters, including the symbiotically regulated nif D and nif H promoters of Bradyrhizobium japonicum. The root nodules formed by B. japonicum transconjugants containing a single copy per genome of a nitrogenase promoter-lux AB fusion emit light of sufficient intensity to be detectable by the dark-adapted eye. Promoter-lux AB fusions can be detected and quantified in vivo with a high signal-to-noise ratio in unrestricted host background without noticeable effect on the growth or viability of the cultures.

V. harveyi luciferase is a heterodimer (alpha beta) encoded by two cotranscribed genes (lux AB) of approximately 2.0 kb in size (Baldwin, T. O., Berends, T., Bunch, T. A., Holzman, T. F., Rausch, S. K., Shamansky, L., Treat, M. L. & Ziegler, M. M. (1984) Biochemistry 23, 3663–3667). A 4.0 kb HindIII fragment containing the lux AB genes of V. harveyi was cloned into pBR322 (pTB7) and shown to be expressed in E. coli (Baldwin, T. O., Berends, T., Bunch, T. A., Holzman, T. F., Rausch, S. K., Shamansky, L., Treat, M. L. & Ziegler, M. M. (1984) Biochemistry 23, 3663–3667.) from the Pl (anti-Tet) promoter (Stuber, D. & Bujard, H. (1981) Proc. Natl. Acad. Sci. USA 78, 167–171). The nucleotide sequence of lux AB indicated that the alpha and beta subunits have molecular weights of 40,108 and 36,349, respectively, even though their migration in SDS-polyacrylamide gels showed sizes of 42,000 and 37,000 daltons. Reference is made to the following publications: Cohn, D. H., Mileham, A. J., Simon, M. I., Nealson, K. H., Rausch, S. K., Bonam, D. & Baldwin, T. O. (1985) J. Biol. Chem. 260, 6139–6146; and Ziegler, M. M. & Baldwin, T. O. (1981) Curr. Top. Bioenergy. 12, 65–113. The single active center resides primarily, if not exclusively, on the alpha subunit but both subunits are required for activity (Ziegler, M. M. & Baldwin, T. O. (1981) Curr. Top. Bionerg. 12, 65–113). Bacterial luciferuse catalyzes the flavin-mediated hydroxylation of a long-chain aldehyde to yield the carboxylic acid and an excited flavin; the flavin decays to ground state with the concomitant emission of light (lambda max=490 nm). The overall reaction is shown below.

Luciferase

Colonies expressing luciferase genes emit blue-green light upon exposure to aldehyde substrate. The bioluminescence can be detected either visually or by photography with Polaroid films, and it can be quantified by densitometry of X-ray films, with a photomultiplier photometer, or in a scintillation counter.

Strains, Plasmids and Plant Material. Bradyrhizobium japonicum USDA strain 110 was provided by A. Eaglesham (Boyce Thompson Institute). E. coli strains used were HB101, JA221, and SM10. Reference is made to the following publications: Boyer, H. W. & Roulland-Dussoix, D. (1969) J. Mol. Biol. 41, 459–472; Clarke. L. & Carbon, J. (1979) Gene 5, 111–126; and Simon, R., Priefer, U. & Puhler, A. (1983) in Molecular Genetics of the Bacteria-Plant Interaction, Puhler, A., ed. (Springer, Berlin), pp. 98–106. Plasmid pMR19 was derived from pJN13 by moving mob genes from the EcoRI site to BamHI, thus restoring chloramphenicol resistance, and leaving a single HindIII site located in the middle of a 13 kb chormosomal fragment from B. japonicum. Soybean (Glycine max, var. Wilkin) seeds were inoculated and plants grown in a controlled environment as described by Jagadish and Szalay (Jagadish, M. N. & Szalay, A. A. (1984) Mol. Gen. Genet. 196, 290–300). Nodules were excised, weighed and tested for nitrogen fixation. Plasmid pMR19 is on deposit as identified herein above.

Plasmid Constructions. Plasmids pFIT001 and pPALE001 are derivatives of pBR322. The lux AB gene cluster of Vibrio harveyi was from pTB7, and the restriction sites HindIII, EcoRI and SalI were made unique as shown in FIG. 1. The neomycin phosphotransferase gene (Km) was excised from pREV1000 with HindIII-AvaI and cloned into a BglII site of pPALE001 by blunt-end ligation. In the construction of pPALE001, a 0.6 kb SalI-HindIII fragment of pBR322 and a 0.3 kb HindIII-KalI fragment of V. harveyi DNA were deleted to form a single promoter-cloning site, SalI, located about 130 bp upstream from the translational initiation codon of lux A. Even though the Pl promoter of pBR322 was deleted from pPALE001, the resulting plasmid expressed detectable bioluminescence at about 1% the level of pTB7. To eliminate this read-through from upstream sequences, trp A transcription terminator (Christie, G. E., Frarnham, P. J. & Platt, T. (1981) Proc. Natl. Acad. Sci. USA 78, 4180–4184) was ligated into the XmaIII site of pPALE001 located about 0.3 kb upstream of the promoter-cloning site.

E. coli-Rhizobium Conjugations. Mobilizable plasmids carrying the lux AB genes and the origin of transfer (ori T or mob) fragment were conjugated from E. coli strain SM10 to Bradyrhizobium japonicum strain 110 on TY plates as described in the publication by Jagadish, et al. further identified hereinabove. Transconjugants were selected on Rhizobium minimal media containing antibiotics at 30° C.

Detection of Bioluminescent Colonies on Agar Plates. Luciferase activity in an E. coli or Bradyrhizobium colony in the presence of n-decanal (n-decyl aldehyde, Sigma) vapors was detected visually in a photographic darkroom within 10–60 seconds. A single streak of n-decanal was made on the inside of the Perti dish lid using a Q-tip. For a permanent record, colonies were photographed on Polaroid type 57 film (see legend to FIG. 2) or exposed to an X-ray film. For the latter, colonies were first transferred to a sterile nitrocellulose filter as if they were to be processed for colony hybridization. The filter was placed on the bottom of a plastic Petri dish, covered with a lid moistened with n-decanal, and directly exposed to X-ray film at room temperature (see also Luxdot Assay).

Luxdot Assay. *E. coli* or *Bradyrhizobium* cells were grown in liquid media to mid or late log phase, and about 1-5 ul volumes ($10^7$–$10^8$ cells) were pelleted by centrifugation. Cells were resuspended in 0.1 ml of water on ice, and dilutions were made in water to inhibit cell division. Following the determination of cell number with a hemocytometer, 5 ul droplets of each dilution were placed on the bottom of an empty Petri dish. A streak of n-decanal was applied to the inner side of the lid and the covered Petri dish was exposed to an X-ray film at room temperature. The exposure time varied between a few seconds and several hours, depending on the promoter strength, the copy number of the promoter-lux AB gene fusion, and the number of cells in a droplet.

Luciferase Assays In Vivo and In Vitro. Luciferase activity was measured using a photomultiplier photometer (Hastings, J. W., Baldwin, T. O. & Nicoli, M.Z. (1978) Methods Enzymol. 57, 135-152) with the sensitivity of $9.8 \times 10^9$ quanta $\sec^{-1}$ (light unit)$^{-1}$, referenced to the light standard of Hastings and Weber (Hastings, J. W. & Weber, G. (1963) J. Opt. Soc. Am. 53, 1410-1415). The substrate used for both types of assay was a sonicated suspension of 50 ul of n-decanal in 100 ml of 0.9M NaCl, prepared fresh. Assays in vivo were carried out by mixing quickly 1 ml of cell culture with 1 ml of the substrate suspension and measuring the peak value of the emitted light.

For assays in vitro, cultures (0.5 ml) were centrifuged in Eppendorf tubes and the pellets frozen at $-20°$ C. Cells were resuspended in 50 ul of 10 mM EDTA, 1 mM DTT, pH 7.0, and sonicated on ice. The reaction mixture consisted of 10ul of the sonicated cell extract, 1 ml of the assay buffer (0.2% BSA in 50 mM phosphate buffer, ph 7.0), 10 ul of the aldehyde substrate suspension, and 1-1.5 ml $FMNH_2$ (reduced by $H_2$ with 10% Pt on activated carbon).

Measurements of Bioluminescence in a Liquid Scintillation Counter. Absorbance of log phase cultures was first measured at 600 nm to determine the approximate cell number. A 1-10 ul volume of the culture ($1.5 \times 10^4 - 1.5 \times 10^5$ cells) was pipetted into a scintillation vial containing 1 ml $H_2O$ and 50 ul of the sonicated n-decanal solution, prepared as described above, and the light was measured in the 32p channel. The peak value was recorded within 1 to 2 minutes, or less if more n-decanal solution was used.

Figure 1B:
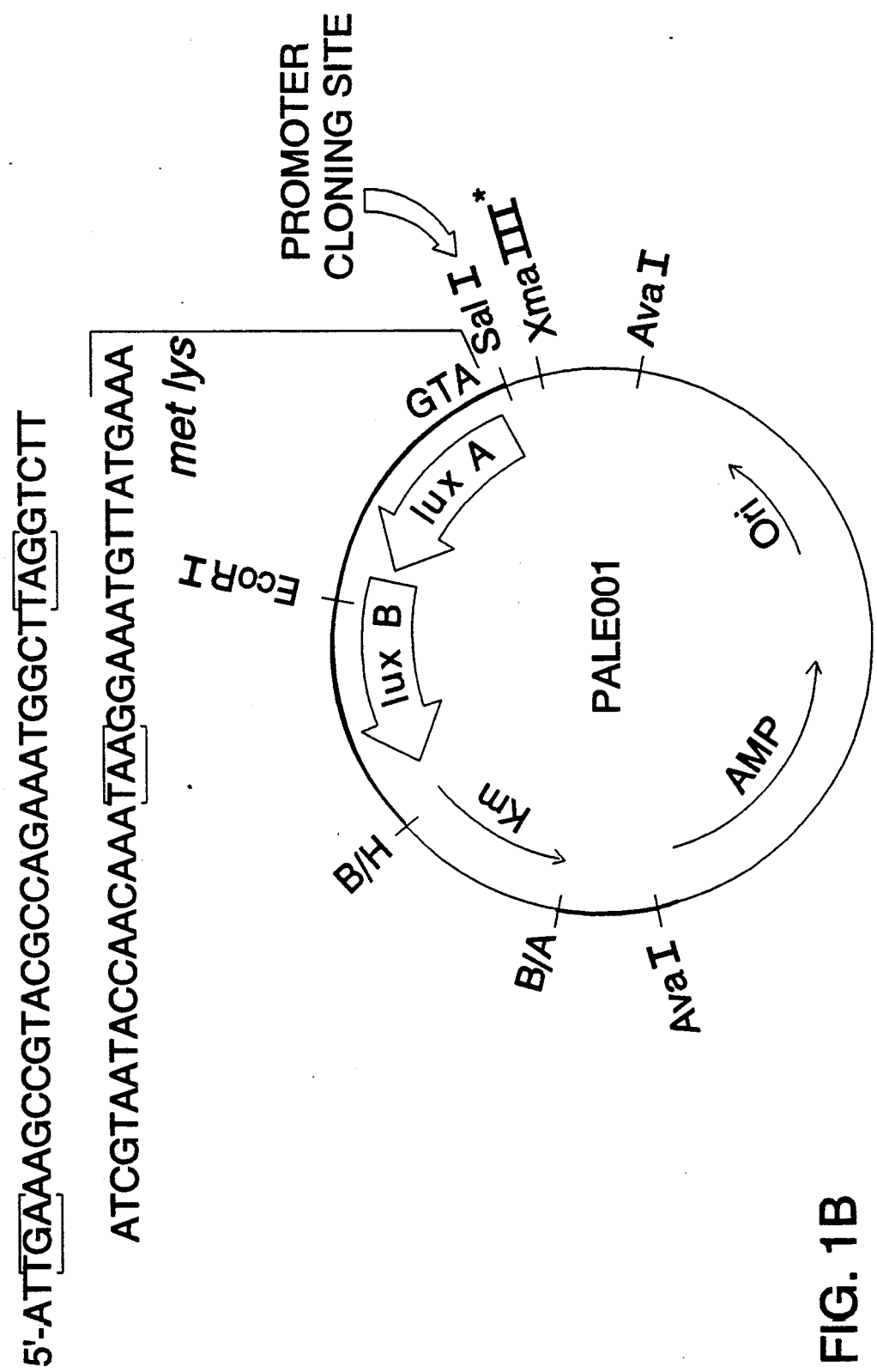
Figure 1C:
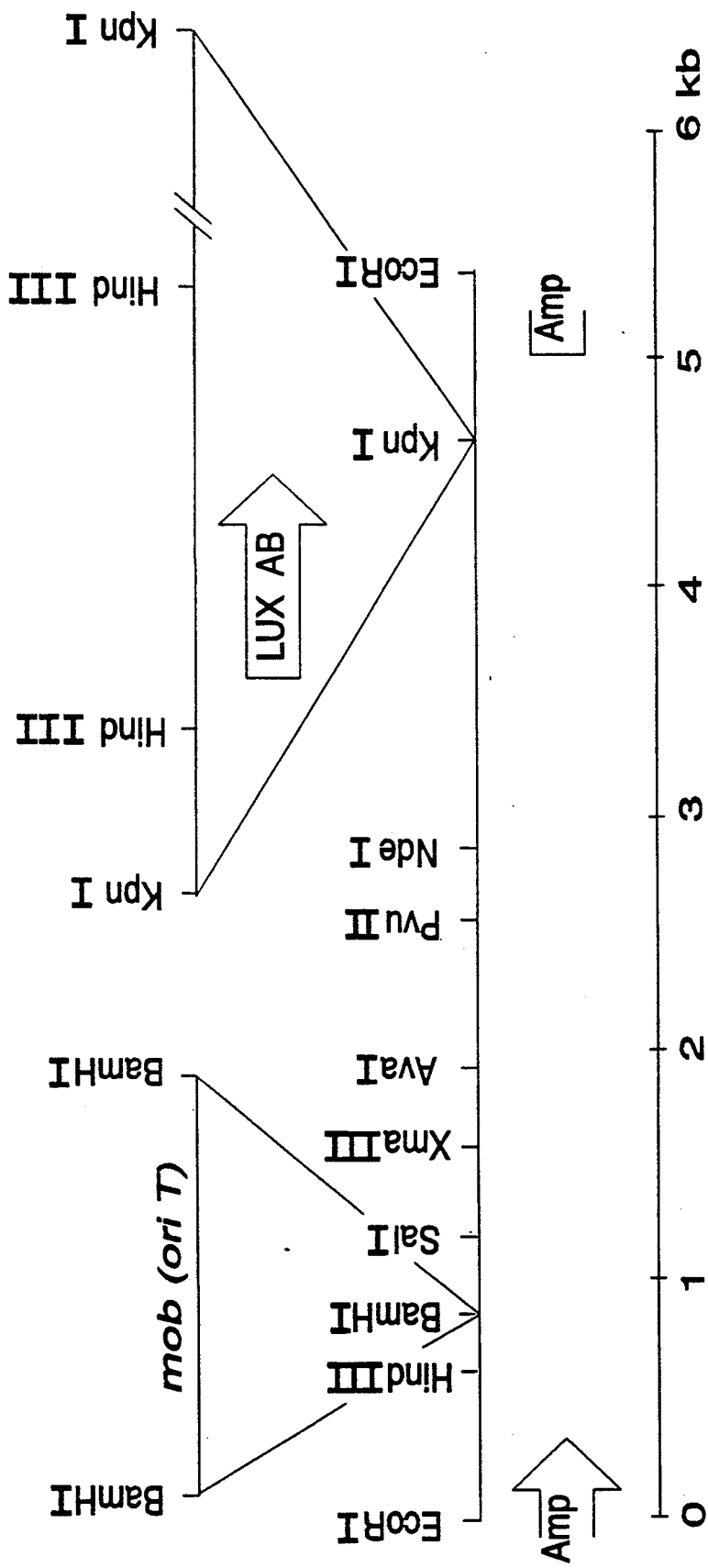

FIGS. 1A and 1B show the plasmid vectors, pFIT001 and pPALE001 respectively. Following the insertion of *V. harveyi* DNA (heavy line), the EcoRI and HindIII sites of pBR322 downstream of the cloned fragment were inactivated by blunt-end ligation. The 70 bp nucleotide sequence upstream of the ATG indicated in pPALE001 contains translational stop codons (brackets) in all 3 translational reading frames. The asterisk at the XmaIII site of pPALE001 indicates that this restriction site has been inactivated by blunt-end instertion of a trp A transcription terminator. B/H and B/A indicate sites of blunt-end ligation of a HindIII-AvaI fragment containing the neomycin phosphotransferase gene (Km) into a BglII site of pPALE001.

Figure 2A:
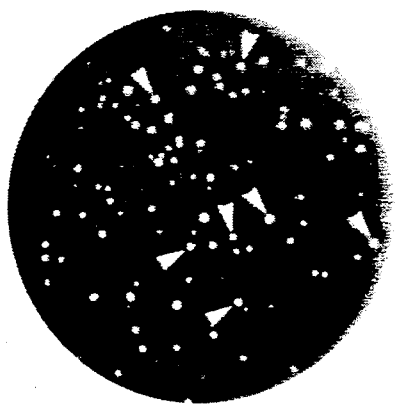
FIGS. 2A, 2B, 2C, 2D and 2E are separate panels illustrating the visual identification of plasmid clones containing inserts using pFIT001.
Figure 2B:
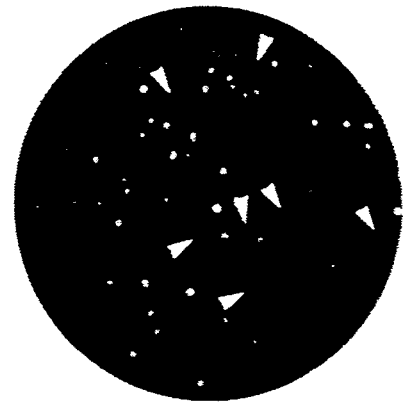
Figure 2C:
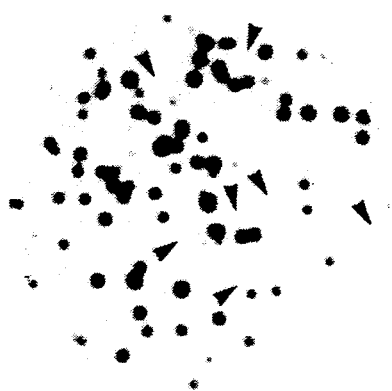
Figure 2D:
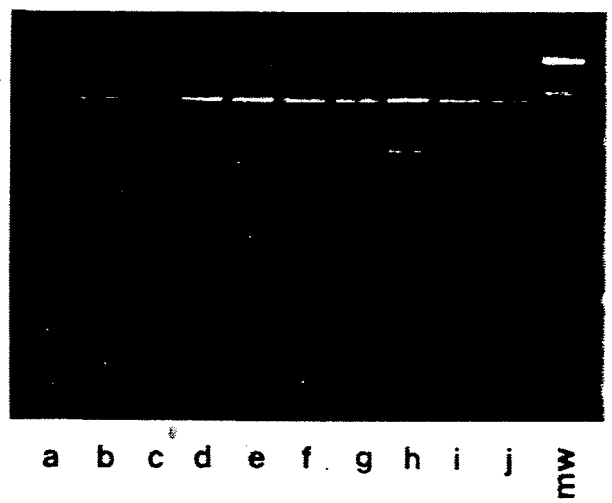

FIGS. 2A, 2B, 2C, 2D and 2E provide visual identification of plasmid clones containing inserts using pFIT001. *E. coli* strain HB101 clones harboring pFIT001 with and without inserts were grown on an ampicillin-containing agar plate and photographed. The FIG. 2A agar plate was treated with n-decanal and photographed on Polaroid type 57 film in the dark with an object-to-lens distance of 40 cm, 15 minute exposure, and an f-stop of 4.5 (FIG. 2B). A nitrocellulose replica of the colonies was also exposed to an X-ray film for 15 seconds and is photographed in the panel. Arrowheads in panels FIGS. 2A, 2B, and 2C indicate some of the dark colonies, i.e. colonies that did not show bioluminescence. The panels in FIG. 2D shows an EcoRI digest of plasmid DNA isolated from 3 bright colonies (lanes a-c; no inserts) and 7 dark colonies (lanes d-j, all contain inserts). Total protein isolated from all of the above clones was analyzed in a 15% acrylamide-1% (w/w) bisacrylamide gel containing SDS (Laemmli, U.K. (1970) Nature New Biol. 227, 680-685) (panel E). The arrow indicates the position of the 37 kb beta subunit of luciferase which is present in the bright colonies (lanes a-c) but absent from the dark colonies (lanes d-j). The 42kd $\alpha$ subunit comigrates with the *E. coli* elongation factor EFTu and its presence in lanes a-c was detected using antibodies to purified luciferase (see also FIG. 4C). Lane cont. shows protein isolated from *E. coli* HB101 containing pBR322; lane mw=molecular weight standards.

Figure 3C:
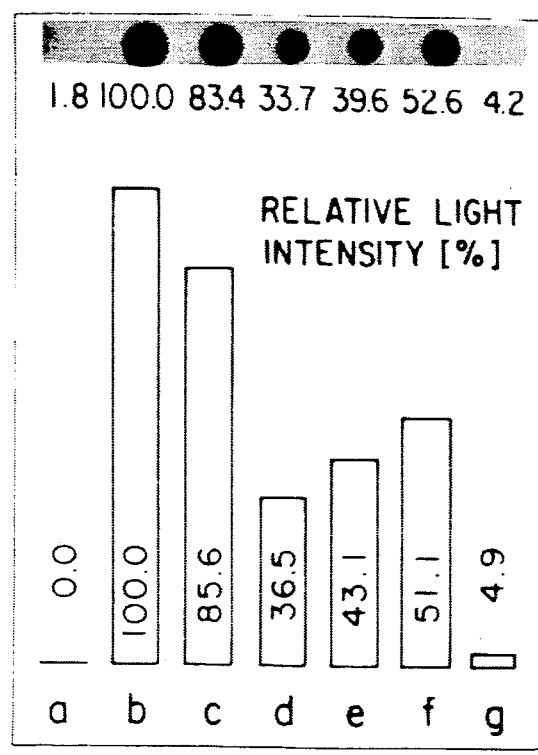

FIGS. 3A, 3B, 3C and 3D illustrate the methods used to monitor gene expression by bioluminescence. The P1 promoter-lux AB gene fusion of pFIT001 was opened at the HindIII site, different DNA fragments known to be devoid of transcription termination signals inserted, and the bioluminescence of cells carrying each construction determined. The panel in FIG. 3A shows a BamHI digest of: pFIT001 (a), pFIT001 carrying different DNA fragments (b-e; see text for descriptin of fragments), pFIT001 carrying a 28 bp trp A transcription terminator (f) and molecular weight markers (g). Luxdot assay performed on *E. coli* containing the above constructs (panel of FIG. 3B, 90 sec exposure) shows that cells carrying pBR322 do not express bioluminescence (cont.) while the expression of lux AB from the P1 promoter (a) is attenuated to varying degrees by different DNA fragments (b-e) and inhibited to about 5% level (see panel C) by the trp A transcription terminator (f). Panel C shows a part of the same luxdot pattern after a 30 second exposure to X-ray film. Relative densitometric scanning data, shown below each dot, and the liquid scintillation counter data, shown in the bar graph, are expressed as percentage of the activity measured for pFIT001. The bar graph in panel D shows the results of the luciferase enzyme assays performed in vitro (open bars) and in vivo (dotted bars) on the same clones. The numbers refer to light units per $2.4 \times 10^7$ cells, with one light unit equal to $9.8 \times 10^9$ quanta/sec.

FIG. 4 shows measurements of acetylene reduction (A) and bioluminescence (B) in soybean nodules formed by the wild-type strain of *B. japonicum* (open bars) and by the transconjugant strain containing the nif D promoter-lux AB gene fusion (hatched bars). Soybeans were transferred to nitrogen-rich medium at day 18 after inoculation and both assays were performed every 12 hours for 4 days. Panel C shows an SDS-polyacrylamide gel containing total bacteroid proteins from nature wild-type (a) and bioluminescent (b) nodules (Coomassie blue stain). After the addition of nitrate, bacteroids were isolated every 12 hours (panel D, lanes 0–84 hr) and their total protein extracts electrophoresed, transferred to nitrocuellulose, and reacted with an antiserum against purified luciferase. Antigen-IgG complexes were visualized using a goat anti-rabbit serum conjugated with peroxidase (Boehringer Mannheim). Lane wt bacteroids from wild-type nodules; a and b=alpha and beta subunits of luciferase.

Figure 5:
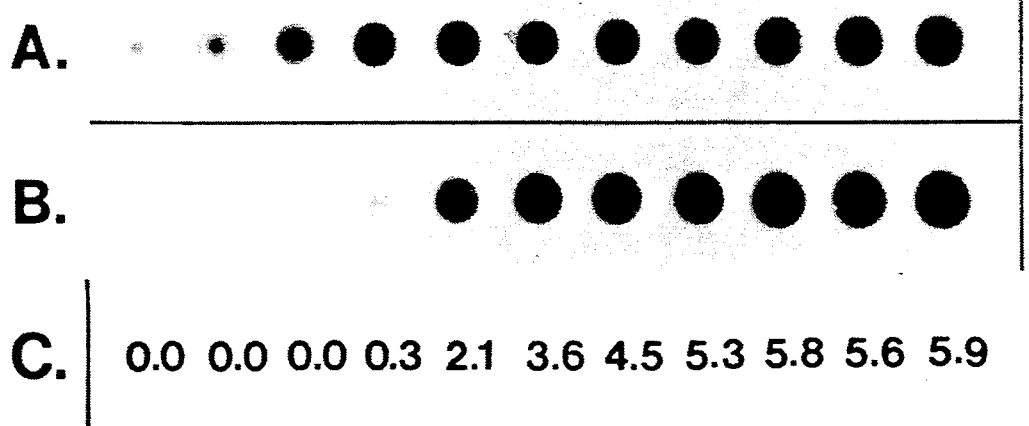
FIG. 5 illustrates the expression of bioluminescence in soy bean nodules controlled by a constitutively expressed P1 promoter (A) and the symbiotically regulated nif D promoter (B) as monitored by the luxdot assay on x-ray film.

FIG. 5 illustrates expression of bioluminescence in soybean nodules coontrolled by a constitutively expressed Pl promoter (A) and the symbiotically regulated nif D promoter (B), as monitored by the luxdot assay on X-ray film. Five ul droplets of total nodule extracts (0.1 g nodule per 0.5 ml of the assay with buffer were exposed to X-ray film in the presence of n-decanal vapors. The increase in luxdot intensity in panel A is due to an increase of the bacteroid number from about $1 \times 10^7$/mg tissue on day 7 to approximately $1.5 \times 10^{10}$/mg on day 14, as determined in a hemocytometer. Panel C shows nitrogen fixation activity in the bioluminescent nodules measured prior to their homogenization.

Visual Identification of Plasmid Clones Containing Inserts Using pFIT001. Identification of bacterial clones carrying DNA inserts has generally been accomplished by targeting inserts into a gene encoding either antibiotic resistance or a marker enzyme (e.g. lac Z) and subsequently screening for antibiotic sensitivity or a phenotype (e.g., blue/white colonies on X-gal plates), or through a miniprep isolation and electrophoretic analysis of plasmid DNA from individual clones. The use of the vector pFIT001 allowed us to detect easily by eye all colonies carrying inserts and distinguish them from colonies containing the parent plasmid.

Figure 2E:

The Pl promoter-lux AB gene fusion was found to be constitutively expressed in all E. coli and B. japonicum strains tested. To demonstrate its use in a rapid identification of colonies containing plasmids with inserts, the pFIT001 plasmid was linearized with EcoRI and ligated to about 30% insertion frequency (Dugaiczyk, A., Boyer, H. W. & Goodman, H. M. (1975) J. Mol. Biol. 96, 171–184) with a small population of DNA fragments previously digested with EcoRI. Since the EcoRI site of pFIT001 is located in the lux AB gene (FIG. 1A), which is known to be essential for bioluminescence, the presence of any inserts will result in dark transformants. FIG. 2A shows the pFIT001-containing transformants of E. coli strain HB101 on an agar plate. Following treatment of the same plate with n-decanal vapors, bioluminescent colonies were photographed in the dark (FIG. 2B), and subsequently exposed for about 15 seconds to an X-ray film (FIG. 2C). The arrowheads in panels A, B and C indicate the presence of several colonies that do not emit light. All dark colonies analyzed were shown to carry an EcoRI insert in the pFIT001 vector (FIG. 2D, lanes d–j), while no inserts were found in any of the bioluminescent colonies (FIG. 2D, lanes a–c). Direct evidence for the lack of luciferase in the dark colonies was provided by protein analysis on polyacrylamide gels containing SDS (FIG. 2E).

Measurement of Promoter Strength In Vivo; Luxdot Assay. The use of the plasmid vector pFIT001 has enabled us not only to visually identify plasmid clones containing inserts, but also to detect and quantify changes in the rate of gene expression in intact E. coli or Bradyrhizobium cells. To alter the rate of luciferase expression from the Pl promoter of pFIT001, different DNA fragments free of transcriptional terminators were inserted into the region separating the promoter from lux AB, and the resultant clones were analyzed for bioluminescence. Four DNA fragments representing central protions of selected structural genes were purified by electroelution (Yang, R. C. A., Lis, J. & Wu, R. (1979) Methods Enzymol. 68, 176–182) and blunt-end ligated into the HindIII site of pFIT001. The following fragments were used: a 0.6 kb BamHI-NruI fragment of the tetracycline resistance gene of pBR322 (FIG. 3A, lane b), a 0.85 kb AvaI fragment of stem Rhizobium BTAi1 chromosome isolated from pRL11H (Legocki, R. P., Eaglesham, A. R. J. & Szalay, A. A. (1982) in Molecular Genetics of the Bacteria-Plant Interaction, ed. Puhler, A. (Springer, Berlin), pp. 210–219) (lane c), a 0.5 kb PvuII fragment of the lac Z gene isolated from pXJ003 (lane d), and a 1.1 kb BglII-SalI fragment containing promoterless NPTII gene isolated from transposon Tn5 of pSUP1011 (lane e). Droplets of 5 ul dilutions of E. coli cells transformed with the above plasmids were spotted on the bottom of an empty Petri dish and exposed to an X-ray film in the presence of n-decanal vapors. The luxdot pattern shown in FIG. 3B was obtained after a 90 second exposure to an X-ray film. It is apparent that the intensity of light produced by the uninterrupted Pl promoter-lux AB gene fusion (lane a) is attenuated to varying degrees by the insertion of different DNA fragments (lanes b-e), and that the transcriptional signal can be efficiently blocked by the trp A transcription terminator (lane f). The observed differences in luciferase levels are likely to be due to changes in the 5' region of mRNA's and their translatibility, rather than due to a decreased promoter strength. However, when the Pl promoter of pFIT001 was replaced with other promoter signals, including a synthetic lac promoter (Marians, K. J., Wu, R., Stawinski, J., Hozumi, T., & Narang, S. A. (1976) Nature 263, 744–748), a tac promoter (deBoer, H. A., Comstock, L. J. & Vasser, M. (1983) Proc. Natl. Acad. Sci. USA 80, 21–25), and a B. japonicum promoter library expressable in E. coli, a wide variation in luxdot intensity was observed that could be related directly to promoter strength (data not shown). Similar results to those in E. coli were obtained in Bradyrhizobium japonicum 110, using the Pl promoter-lux AB gene fusions on a wide host range plasmid pSUP106, however, dots of comparable intensity to those shown in FIG. 3B were observed only after about 30 minute exposure to X-ray film.

Our data indicated that a luxdot assay can be quantified very simply by two methods, and that the results obtained are in agreement with the luciferase enzyme assays in vivo and in vitro. FIG. 3C shows a part of the same luxdot pattern generated by $1.6 \times 10^6$ cells in each 5 ul droplet, followed by a 30 second exposure to X-ray film. The film was scanned (Quick, Scan R&D, Helena Laboratories), and data computed using an Apple IIe computer with an Applegration II program. Numbers shown under the luxdot pattern in FIG. 3C represent the relative strength of lux expression in each clone with reference to the original pFIT001 construct (100% activity), used as an internal standard. Based on the luciferase assay carried out in vitro for the clone selected as an internal standard, all relative numbers obtained from a luxdot pattern can be expressed in light units (1 light unit = $9.8 \times 10^9$ quanta/sec). The diagram in FIG. 3C illustrates luciferase expression in the above clones as measured by a liquid scintillation counter, with reference to the same internal standard of pFIT001. The results obtained were consistent with those from the luxdot scanning technique, and could also be related to the actual light units using the selected clone as the internal standard.

Figure 3D:
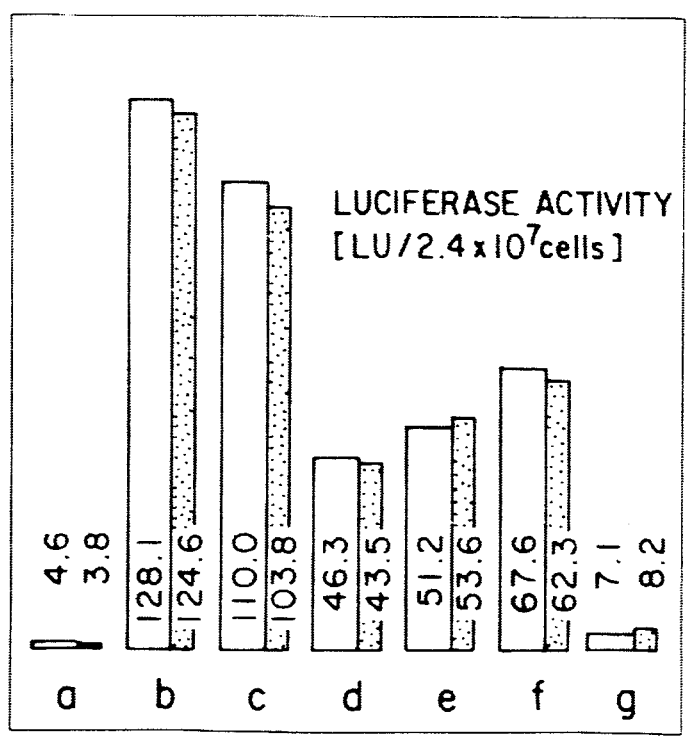

To measure luciferase activity directly, all of the above clones were subjected to the enzyme assays in vitro and in vivo, and the results were expressed in light units (FIG. 3D). It is apparent that all measurements presented in FIG. 3, including the simple scintillation counting method, are in good agreement with the results of the enzyme assay in vitro, and that using just one clone as an internal standard it is possible to convert all data to the actual enzyme units.

Bioluminescence in Soybean Nodules: Expression of Luciferase Genes from nifD and nifH Promoters of *Bradyrhizobium japonicum*. The measurements of nitrogen fixation in free-living diazotrophs and in nodules have been based almost uniquely on the acetylene reduction assay, in which the conversion of acetylene to ethylene by nitrogenase is determined by gas chromatography (Hardy, R. W. F., Holsten, R. D., Jackson, E. K. & Burns, R. C. (1968) Plant Physiol. 43, 1185–1207). We have previously shown in stem nodules of *Aeschynomene scabra* that a chromosomally integrated nif H promoter-lac Z gene fusion in the stem Rhizobium bacteroids is activated in trans with the native nif region. We now report that the activity of nif D and nif H nitrogenase promoters of *Bradyrhizobium japonicum* can be measured in a single root nodule of soybean using liquid scintillation counter, based on bioluminescence.

The nif D promoter region of *B. japonicum* was excised from pAY6 as a 0.8 kb CLaI fragment containing approximately 0.3 kb of the N-terminal region and 0.5 kb of the 5' upstream sequences. The nif H promoter region was located on a 0.75 kb SMaI-XhoI fragment of pAY8 containing approximately 0.3 kb of the N-terminal region and 0.45 kb of the 5' upstream sequences. The nif D and nif H promoter-containing fragments were purified by electroelution, and each blunt-end ligated into the SalI site of pPALE001. As indicated in FIG. 1, plasmid pPALE001 carries a 70 bp sequence of *V. harveyi* containing translation stop codons (brackets) in all three reading frames prior to the ATG codon of lux A. This sequence will block any translational fusion upstream of lux A without causing transcriptional termination.

The nif D and nif H promoter- lux AB fusions were excised from pPALE001 with AvaI (see FIG. 1) and placed in the middle of a 13 kb fragment of *B. japonicum* chromosome, located on a mobilizable plasmid pMR19. Bradyrhizobium transconjugants were selected in the presence of kanamycin, and colonies containing a single copy of the promoter fusion per genome were identified as "double cross-overs" by DNA hybridization, as demonstrated previously in stem Rhizobium BTAil. No bioluminescence was detected in free-living transconjugants containing the nif promoter-luciferase gene fusions, as judged by extended exposures to X-ray film.

Figure 4A:
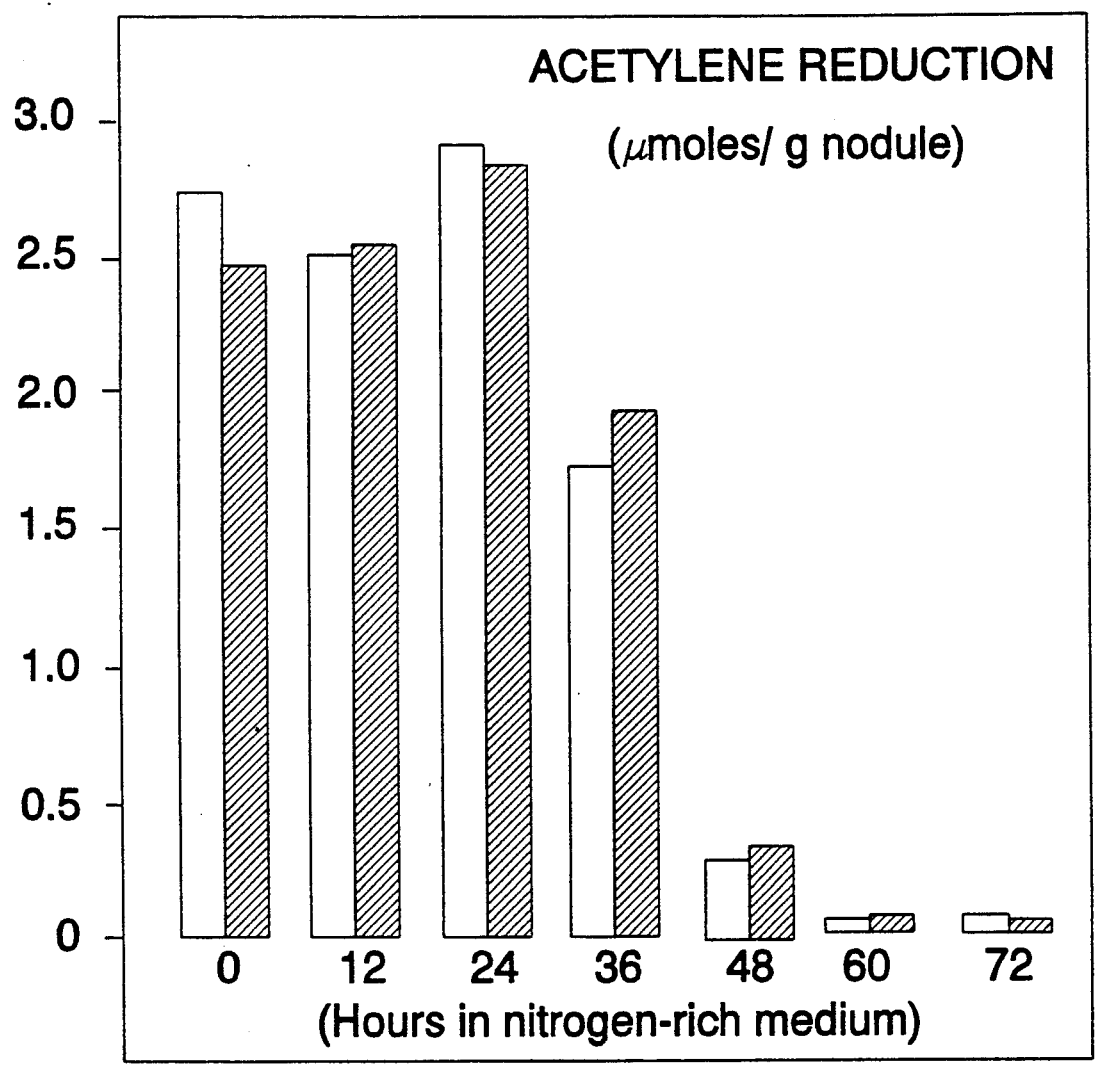
FIGS. 4A, 4B, 4C, and 4D are separate panels depicting plural measurements and/or observations as it relates to the insertion of lux AB genes into the chromosome of *B. japonicum*.
Figure 4B:
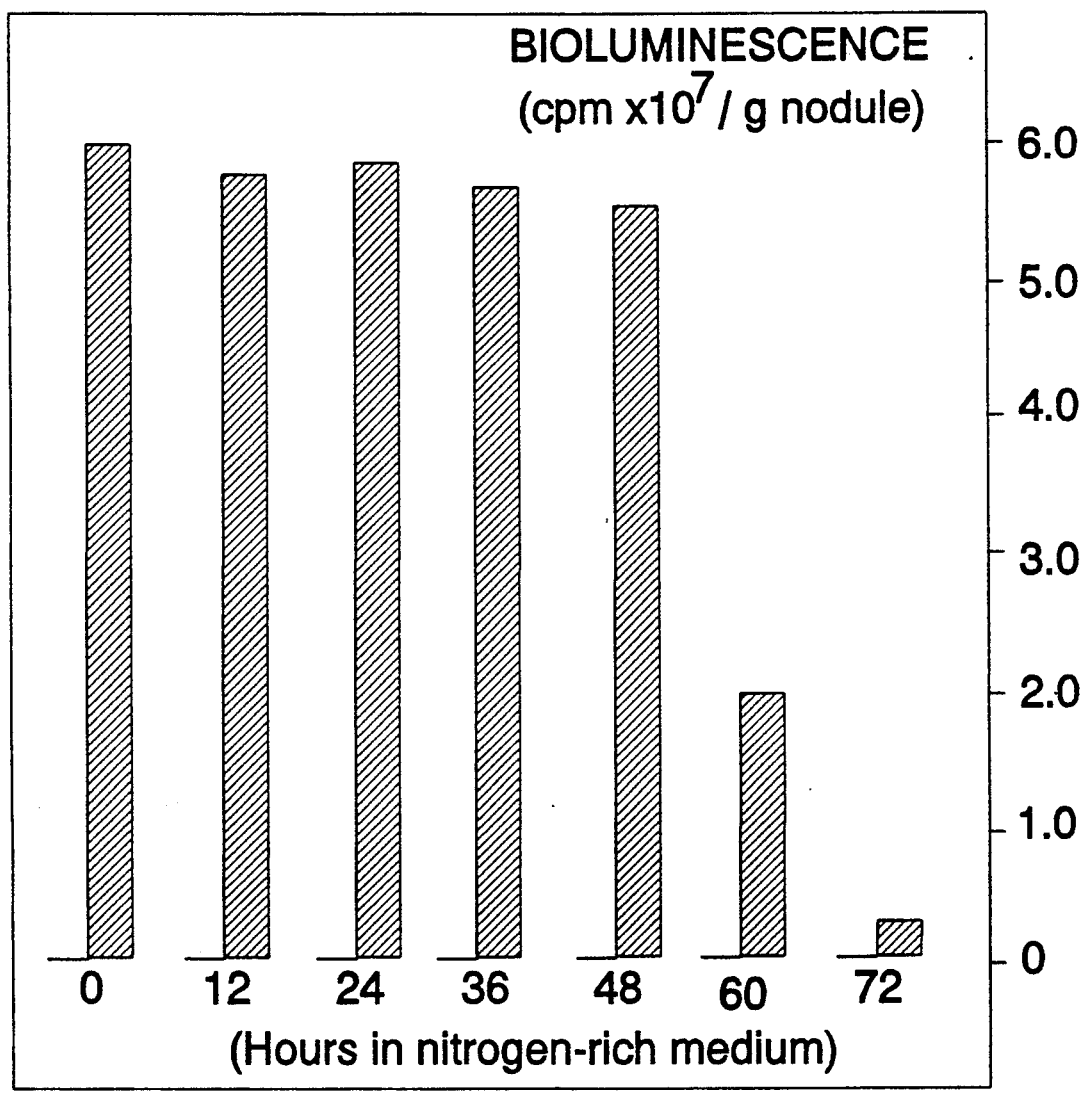

For plant tests, soybeans were divided into three inoculation groups: wild-type, nif D promoter-lux AB fusion, and nif H promoter-lux AB fusion. Beginning at day 18 after inoculation, single nodules were removed from roots, weighed, and measured for acetylene reduction in a 0.5 cc volume of 10% (v/v) acetylene. Each nodule was homogenized in 200 ul of the luciferase assay buffer using a small mortar and pestle, and total extracts were examined for bioluminescence in a liquid scintillation counter. FIG. 4A shows that nodules formed by the wild- type *B. japonicum* and those formed by transconjugants containing the nif D promoter-lux AB fusion fix nitrogen at approximately equal rates. About 36 hr after addition of nitrogen-rich medium (Summerfield, R. J., Dart, P. J., Huxley, P. A., Eaglesham, A. R. J., Minchin, F. R. & Day, J. M. (1977) Exp. Agric, 13, 129–142), which is known to inhibit expression of nif genes in rhizobia, a rapid decline in nitrogen fixation was observed. Measurements of bioluminescence performed on the same tissues (FIG. 4B) showed high levels of luciferase activity in nodules containing the nif D promoter-lux AB fusion and a similar decline of bioluminesce at 60 hr. There was no bioluminescence detected at any stage in the wild-type nodules.

Figure 4C:
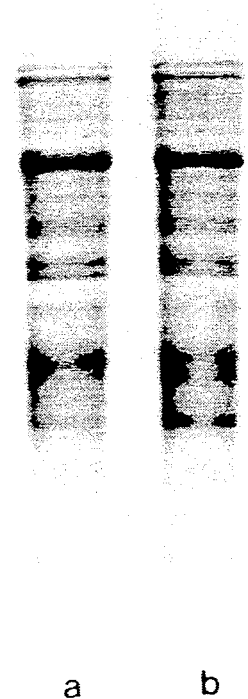
Figure 4D:
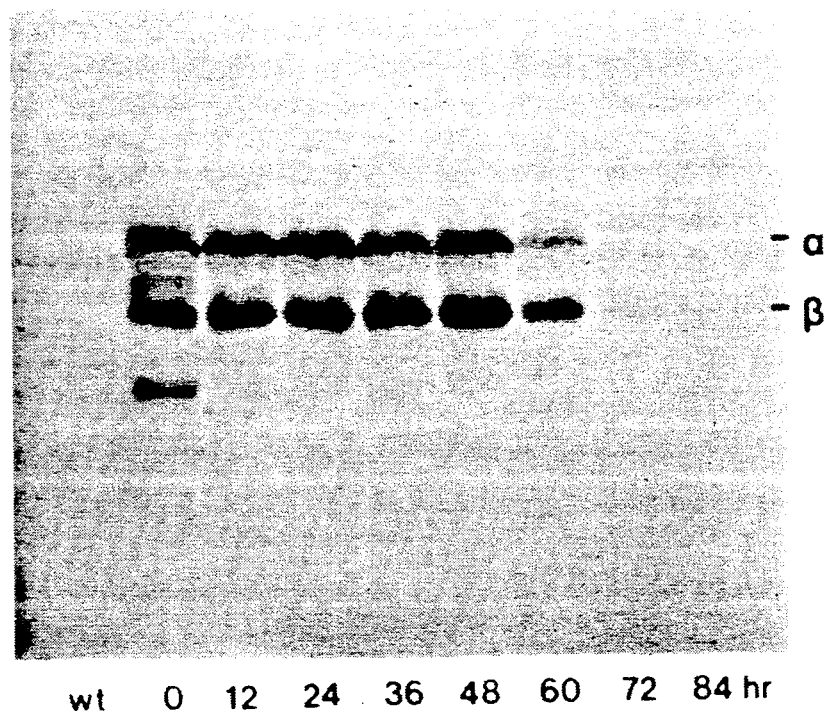

It was not fully understood why the decline in bioluminescence did not coincide with the decline in nitrogen fixation, but rather the two events occured 24 hr apart. In contrast to the nitrogenase complex, the bacterial luciferase from *V. harveyi* has been described as a relatively stable protein, e.g., its structure and enzymatic activity were not affected by repeated freezing and thawing (Hastings, J. W., Baldwin, T. O. & Nicoli, M. Z. (1978) Methods Enzymol. 57, 135–152), and thus it was possible that this protein had a long half-life in *B. japonicum* bacteroids. To determine levels of the luciferase protein in nodules treated with nitrate, bacteroids were isolated at 12 hr. intervals, and their total protein extracts analyzed electrophoretically. FIG. 4C shows that the amount of luciferase in bioluminescent nodules is very small and that its presence cannot be detected by staining. A nitrocellulose replica reacted with antibodies against purified luciferase (FIG. 4D) indicates virtually the same level of the enzyme between 0 and 48 hr following the addition of nitrate, and a steady decrease in the amount of luciferase polypeptides in nodules may indeed be very low, and that the stability of this protein may cause the observed delay in the decline of bioluminescence.

To determine if in the early stages of nodule development the expression of nitrogenase is in fact accompanied by the expression of bioluminescence, total extracts of two types of nodules were compared using the luxdot assay: nodules formed by B. japonicum containing a single chromosomal copy of a P1 promoter-lux AB fusion, and nodules equipped with the nif D promoter-lux AB fusion. It is clear that bioluminescence controlled by the constitutively expressed P1 promoter is detectable even in very young nodules (7 days after inoculation, FIG. 5A), whereas expression of bioluminescence is in nodules containing the nif D promoter-lux AB fusion occurs only at 3to 4 days later (FIG. 5B), and it coincides with the nitrogenase activity (FIG. 5C). The initiation of nitrogen fixation in soybean nodules at day 10 of the symbiosis is consistent with previous publications (Bergersen, F. J. & Goodchild, D. J. (1973) Australian J. Bio. Sci. 26, 729–741), and the appearance of bioluminescence at that time shows that the nif D promoter-lux AB fusion is activated coordinately with the native nif locus of *B. japonicum*.

It is interesting to note that while bioluminescence in total extracts from wild-type nodules showed on the average 30–40 cpm per nodule, the same size nodule containing the nif D promoter-lux AB fusion showed typically a peak value of as much as $6 \times 10^7$ cpm. Bioluminescence in these nodules in the presence of n-decanal vapors was visible to the naked eye, but only if the tissue was cut open. Similar results to those shown in FIG. 4 were obtained for nodules containing the nif H promoter-lux AB fusion (data not shown).

It is also noteworthy that extracts from a single nodule containing one copy of lux AB per bacteroid yielded as much as $2.0-9.0\times10^5$ cpm in a liquid scintillation counter without addition of exogenous aldehyde. These results indicated the presence in soybean nodules of aldehyde(s) that can serve as substrate for the bioluminescence reaction. The levels of bioluminescence are two orders of magnitude lower than those with n-decanal added exogenously, but nevertheless, the observation is worthy of further study.

Bacterial luciferase genes lux AB from *V. harveyi* may become an extremely useful tool for studying procaryotic gene expression. The lux AB gene system appears to have several distinct advantages over the lac Z system. First, the luciferase appears to function in any host background and in any growth medium tested. Second, the activity of the enzyme can be visually detected in vivo within a few seconds of exposure to aldehyde vapor, and permanent records useful for quantitation can be made quickly by either direct exposure to X-ray film or by photographic methods. Finally, the range of sensitivity of bioluminescence systems is unparalleled by systems that utilize chromogenic substrates. With a simple photomultiplier photometer (Mitchell, G.W. and Hastings, J.W. (1971) Anal. Biochem. 39, 243-250), it is possible to detect and quantify light from as little as a few femtomoles of luciferase, corresponding to picogram amounts of enzyme. Using E. coli strain SM10 transformed with pFIT001, the luxdot assay has allowed us to detect as few as $10^4$ cells after 15 minute exposure to X-ray film. One feature unique to the bacterial luciferase system is that the substrate for the reaction, n-decanal, is a volatile aldehyde whose vapors rapidly penetrate cell membranes and stimulate bioluminescence in vivo. It is thus possible to detect and quantify the luciferase activity in living cultures without perturbing the living system. This cannot be accomplished using the firefly luciferase system from Photinus pyralis which utilizes firefly luciferin (DeWet, J.R., Wood, K.V., Helinski, D.R. & DeLuca, M. (1985) Proc. Natl. Acad. Sci. USA 82, 7870-7873). Luciferin does not readily pass membranes, and may require some carrier such as DMSO to facilitate permeability, and hence its use appears to be restricted to measurements in vitro using homogenized extracts.

Although a comparison between the lac Z gene of *E. coli* and the lux AB gene cluster of *V. harveyi* as gene expression markers indicates some important advantages to the latter, both systems use the indirect approach of measuring gene expression via enzyme activity (beta- galactosidase and luciferase, respectively), that may not reflect quantitatively the transcriptional events. Nevertheless, the validity of a general approach using promoterless lac Z or NPTII (neomycin phosphotransferase) genes to quantify promoter strength through enzyme assays, has been widely documented using plasmids, phage molucules and chromosomally integrated gene fusions.

The use of pFIT001 and pPALE001 plasmid vectors presented here is based on the fusion of lux AB genes with constitutively expressed or symbiotically regulated promoter regions. In contrast to the recently described expression vector Mini-Mu lux (Engebrecht, J., Simon, M., & Silverman, M. (1985) Science 227, 1345-1347) that involves the use of the entire lux cluster of *V. fischeri* in *E. coli*, the above constructs harbor luciferase structural genes only and require addition of the aldehyde substrate exogenously.

Measurements of bioluminescence in soybean nodules demonstrated that the expression of a single copy per *B. japonicum* genome of the nif D or nif H promoter- lux AB fusion can be detected in a liquid scintillation counter using only a fraction of a single nodule extract. Parallel measurements of nitrogen fixation and bioluminescence carried out on the same nodules prior to and after treatment of plants with nitrate suggested that the expression of nitrogenase and luciferase genes in these nodules is controlled coordinately. It is important to note that while the beta-galactosidase enzyme assay performed on stem nodules involved a significant plant background, measurements of Bradyrhizobium bioluminescence in soybean nodules were completely unaffected by the presence of plant tissue. The lack of plant background to the luciferase system in nodules was apparent during the measurement of bioluminescence in extracts from the wild-type nodules and the nodules formed by bradyrhizobium transcon jugants that contained lux AB genes fused to the nif D or nif H promoter regions in the opposite (wrong) orientation. Nodules from both plant groups showed normal nitrogen fixation activities, but virtually no bioluminescence.

As mentioned hereinabove, bioluminescence in nodules containing nif D promoter- lux AB fusion was strong enough to be visible to the dark-adapted eye, but only if the nodules were cut open. This may be due to two factors related to nodule structure. The light generated by bacteroids, located in the central cortex, could be blocked by several uninfected cell layers of the peripheral cortex and/or the luciferase reaction, known to require oxygen, is enhanced upon exposure of bacteroids to atmospheric oxygen.

The discussion herein focuses on the isolation of symbiotically regulated promoters of *B. japonicum* using promoter- lux AB gene fusions. However, due to the high sensitivity and overall simplicity of the bacterial luciferase assay, it may be possible to detect and monitor activities of even weak promoter signals in single nodules throughout the development of the symbiotic process, as well as in very early stages of nodulation. Rhizobia carrying constitutively expressed luciferase genes will also be extremely useful for competition and localization analysis of nodule initiation.

The foregoing description has been directed to particular embodiments of the invention in accordance with the requirements of the Patent Statutes for the purposes of illustration and explanation. It will be apparent, however, to those skilled in this art that many modifications and changes will be possible without departing from the scope and spirit of the invention. It is intended that the following claims be interpreted to embrace all such modifications and changes.

We claim:

1. An aerobic or facultative anaerobic microorganism which is capable of homologous recombination, transformed by the integration of an isolated foreign DNA fragment, within any of its chromosomal regions, wherein integration of transforming DNA does not alter cell viability, said foreign DNA fragment comprising lux AB genes of any vibrio bioluminescent bacterium fused in operable linkage with an active promoter, and further comprising an antibiotic resistance marker, wherein said active promoter is selected from the group consisting of constitutive promoters of gene expression and inducible promoters of gene expression, and is active in the transformant.

2. The transformant of claim 1 wherein that microorganism is *B. japonicum*.

3. The transformant of claim 1 wherein that microorganism is Rhizobium.

4. The transformant of claim 1 wherein the stable expression of the lux AB genes results in the production of luciferase enzyme which, in turn emits light in the presence of aldehyde vapor as an indication of gene expression and serves as a marker or tag for the transformant.

5. The transformant of claim 1 wherein the expression of the lux AB genes results in the production of luciferase enzyme which, in turn emits light in the presence of aldehyde vapor as an indication of gene expression and serves as a marker or tag for the transformant.

6. The transformant of claim 5 wherein said transformant is cultured in a growth medium known to support growth of the host microorganism in its unmodified form.

7. The plasmid vector pFIT001 as deposited at Agriculture Research Service under accession number NRRL B-18080.

8. The plasmid vector pPALE001 as deposited at Agriculture Research Service under accession number NRRL B-18082.

9. The plasmid vector pMR19 as deposited at Agriculture Research Service under accession number NRRL B-18081.

10. A method of stably modifying a microorganism using bacterial luciferase genes lux AB from any vibrio bioluminescent bacteria, comprising the steps of:
    (a) selecting an aerobic or facultative anaerobic microorganism which is capable of homologous recombination,
    (b) transforming the selected microorganism, by conjugation, with an isolated chromosomal DNA fragment derived from the selected microorganism, said isolated foreign DNA fragment comprising lux AB genes of any vibrio bioluminescent bacterium fused in operable linkage with an active promoter, and further comprising an antibiotic resistance marker, wherein said active promoter is selected from the group consisting of constitutive promoters of gene expression and inducible promoters of gene expression, and is active in the transformant,
    (c) placing said transformant in a growth medium, and
    (d) exposing said transformant to aldehyde vapor such that the resulting bioluminescence in vivo provides an identification of the presence of said transformant.

11. A method of stably modifying a microorganism using bacterial luciferase genes lux AB from any vibrio bioluminescent bacterium, comprising the steps of:
    (a) selecting an aerobic or facultative anaerobic microorganism which is capable of homologous recombination,
    (b) transforming the selected microorganism, by electroporation, with an isolated chromosomal DNA fragment derived from the selected microorganism, said isolated foreign DNA fragment comprising lux AB genes of any vibrio bioluminescent bacterium fused in operable linkage with an active promoter, and further comprising an antibiotic resistance marker, wherein said active promoter is selected from the group consisting of constitutive promoters of gene expression and inducible promoters of gene expression, and is active in the transformant,
    (c) placing said transformant in a growth medium, and
    (d) exposing said transformant to aldehyde vapor such that the resulting bioluminescence in vivo provides an identification of the presence of said transformant.

12. An aerobic or facultative anaerobic microorganism which is capable of homologous recombination, transformed by the integration of an isolated foreign DNA fragment, within any of its chromosomal regions, wherein integration of transforming DNA does not alter cell viability, said foreign DNA fragment comprising lux AB genes of any vibrio bioluminescent bacterium fused in operable linkage with an active promoter, wherein said active promoter is selected from the group consisting of constitutive promoters of gene expression and inducible promoters of gene expression, and is active in the transformant.

* * * * *